US009643020B2

(12) United States Patent
Goldman et al.

(10) Patent No.: US 9,643,020 B2
(45) Date of Patent: May 9, 2017

(54) FEEDTHROUGH ASSEMBLY FOR AN IMPLANTABLE MEDICAL DEVICE

(71) Applicant: Medtronic, Inc., Minneapolis, MN (US)

(72) Inventors: Simon E. Goldman, St. Louis Park, MN (US); Rajesh V. Iyer, Eden Prairie, MN (US); Curtis E. Burgardt, Sauk Rapids, MN (US); Zhi Fang, Maple Grove, MN (US); Michael J. Galloway, Blaine, MN (US); Ryan J. Jensen, White Bear Township, MN (US); James A. Martin, Maple Grove, MN (US); Fabian A. Pena, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 251 days.

(21) Appl. No.: 13/963,103

(22) Filed: Aug. 9, 2013

(65) Prior Publication Data
US 2015/0045862 A1  Feb. 12, 2015

(51) Int. Cl.
*A61N 1/375* (2006.01)
*G01R 31/12* (2006.01)
*H05K 5/02* (2006.01)

(52) U.S. Cl.
CPC ....... *A61N 1/3754* (2013.01); *G01R 31/1227* (2013.01); *H05K 5/0247* (2013.01); *Y10T 29/49004* (2015.01); *Y10T 29/49147* (2015.01)

(58) Field of Classification Search
CPC .............. G01R 31/1221; H05K 5/0247; Y10T 29/49147
See application file for complete search history.

(56) References Cited

U.S. PATENT DOCUMENTS

| 4,678,868 | A | 7/1987 | Kraska et al. |
| 5,175,067 | A | 12/1992 | Taylor et al. |
| 5,735,884 | A * | 4/1998 | Thompson ........... A61N 1/3754 607/36 |
| 5,751,539 | A | 5/1998 | Stevenson et al. |
| 5,817,984 | A | 10/1998 | Taylor et al. |
| 6,396,262 | B2 | 5/2002 | Light et al. |
| 6,414,835 | B1 | 7/2002 | Wolf et al. |
| 6,437,357 | B1 | 8/2002 | Weiss et al. |
| 6,822,735 | B2 | 11/2004 | Kim et al. |
| 6,855,456 | B2 | 2/2005 | Taylor et al. |
| 6,903,268 | B2 | 6/2005 | Marshall et al. |
| 7,064,270 | B2 | 6/2006 | Marshall et al. |

(Continued)

*Primary Examiner* — Peter DungBa Vo
*Assistant Examiner* — Jeffrey T Carley

(57) ABSTRACT

Processes for manufacture and assembly of implantable medical devices are described. In particular, techniques are provided for nondestructive electrical isolation assessment of feedthrough assemblies of the implantable medical devices. The feedthrough assemblies may include an insulating structure, a plurality of terminal pins extending through the insulator and a ferrule having an inner lumen into which the insulating structure is disposed. One or more insulating seals may be disposed at the interface of the ferrule-to-insulating structure and/or the terminal pin-to-insulating structure. The electrical isolation assessments may be based on the dielectric properties of the components of the feedthrough assemblies, such as the insulating structure.

13 Claims, 7 Drawing Sheets

(56) References Cited

U.S. PATENT DOCUMENTS

| | | |
|---|---|---|
| 7,164,572 B1 | 1/2007 | Burdon et al. |
| 7,661,293 B2 | 2/2010 | Dam |
| 7,668,597 B2 | 2/2010 | Engmark et al. |
| 8,160,707 B2 | 4/2012 | Iyer et al. |
| 8,234,942 B2 * | 8/2012 | Sarr ................. G01N 27/82 |
| | | 73/865.8 |
| 8,288,654 B2 | 10/2012 | Taylor et al. |
| 2001/0048305 A1 * | 12/2001 | Borsi ................ G01R 33/385 |
| | | 324/322 |
| 2006/0247714 A1 | 11/2006 | Taylor et al. |
| 2008/0306578 A1 | 12/2008 | Hallander et al. |
| 2011/0106205 A1 | 5/2011 | Reiterer et al. |
| 2012/0279307 A1 | 11/2012 | Prause et al. |
| 2012/0318064 A1 | 12/2012 | Kaack et al. |
| 2013/0034670 A1 | 2/2013 | Hashimoto et al. |
| 2013/0100278 A1 | 4/2013 | Cormier et al. |

\* cited by examiner

FEEDTHROUGH ASSEMBLY FOR AN IMPLANTABLE MEDICAL DEVICE

CROSS REFERENCE TO RELATED APPLICATIONS

Reference is made to commonly-assigned and co-pending application U.S. Ser. No. 13/963,069, filed on even date herewith, entitled "FEEDTHROUGH ASSEMBLY FOR AN IMPLANTABLE MEDICAL DEVICE," which is herein incorporated by reference in its entirety.

TECHNICAL FIELD

The present disclosure pertains to implantable medical devices and in particular to a feedthrough assembly.

BACKGROUND

Applications exist where it may be necessary to penetrate a sealed container with one or more electrical leads or electrical contacts so as to provide electrical access to and from electrical components enclosed therein. One such application may be for an electrochemical cell or for an implantable medical device. Such an implantable medical device may comprise for example, an implantable drug pump, an implantable sensor capsule, a cochlear implant, an implantable pulse generator (IPG) such as those adapted for providing deep brain stimulation, nerve stimulation, electrical pacing therapy and cardiac rhythm management techniques (e.g., for delivering electrical stimulation therapy for various cardiac arrhythmias). In addition, such implantable electronic devices can be used to sense optical signals or deliver optical impulses for stimulation. All such devices, including discrete electrochemical cells, are intended to be covered under the rubric of implantable medical devices.

A typical implantable medical device can have one or more housing or encasement members for isolating the active contents of an electrochemical cell (e.g., battery or capacitor) which can be coupled to one or more electrical components within and/or coupled to the implantable medical device. The implantable medical device typically has at least two major outer housing members that form a hermetically-sealed housing when welded together to provide a hermetically-sealed interior space for the components of the implantable medical device.

Electrical feedthrough assemblies are provided to form a conductive path extending between the interior of the hermetically-sealed housing and the exterior of the housing. The conductive path comprises a conductive pin or terminal that is electrically insulated from the housing. Many feedthrough assemblies, which are known in the art, include the terminal, a ferrule surrounding the terminal, an insulating body such as a glass or ceramic (including alumina) material for positioning and insulating the pin within the ferrule, and an epoxy backfill of the ferrule, over the insulator and around the terminal.

Feedthrough corrosion may be encountered when the feedthrough assembly components come into contact with body fluids or electrolytes, if fluid leak paths form in the backfill or at the interface of the backfill with the terminal and or ferrule. In addition, defects in components of the feedthrough assembly, such as the insulating body, have been observed to result in corrosion.

Conventionally, visual inspection has been used to identify the presence of defects in the feedthrough assembly components. The visual inspection is qualitative and inherently prone to operator error and variation. What is needed is a performance measurement to enable a quantitative electrical isolation assessment.

SUMMARY

The disclosure describes systems and methods for manufacturing a feedthrough assembly of an implantable medical device. The manufacturing includes a non-destructive electrical isolation assessment of the feedthrough assembly, and in particular, assessment to detect defects in the insulating structure of the feedthrough assembly.

In one embodiment, a test probe is disclosed for measuring properties of the feedthrough assembly that provide an indication of the presence of defects. The measured properties may include measurements of dielectric values of the insulating structure. The test probe may include first and second probe leads that electrically couple a control system to first and second electrodes, respectively. The electrodes may be configured to be engageable with a surface of the insulating structure.

In an example, the control system may include an electric field generator and a detector for measuring an electrical property responsive to pulse signals generated by the electric field generator. The generated pulse signal may include a series of a plurality of pulses having one or two polarities. In yet other examples, the generated pulse signal may include a high voltage signal.

In another example, the control system may include an analyzing tool for analyzing the response of a circuit to changes in the properties of the circuit resulting from the coupling of the circuit to the insulating structure. The circuit may include a tuned resonant circuit that includes an inductor, a capacitor and a resistor. In another embodiment, the circuit may be configured to measure the insulation resistance of the insulating structure. In yet another embodiment, the circuit may be configured to measure the dielectric withstanding voltage of the insulating structure.

In another aspect of the disclosure, a method manufacturing a feedthrough assembly includes the tasks of providing an insulating structure having a top portion, a bottom portion and at least one aperture extending from the top portion to the bottom portion, the aperture having a first diameter, providing a ferrule having an outer surface, the ferrule defining an inner lumen surface, disposing the insulating structure within the inner lumen surface to fixedly secure the insulating structure to the ferrule, inserting a terminal pin into the aperture, the terminal pin having a diameter sized to correspond to the first diameter.

In an embodiment, a pulse signal may be applied between the top portion and the bottom portion of the insulating structure, and an electrical parameter measured in response to application of the pulse signal to detect a variation of a dielectric property at two or more portions of the insulating structure.

The measurement of the electrical property may be performed to detect defects in the insulating structure of a feedthrough assembly. In one embodiment, the measurement may be performed by capacitively coupling a tuned resonant circuit with the feedthrough assembly, where variations in the magnitude of the changes to the resonance of the circuit are indicative of variations of the dielectric owing to the presence of defects, and analyzing the changes in the resonance of the tuned circuit.

In another implementation, the measurement may be performed by applying a high voltage signal to the feedthrough assembly and measuring an electrical property in response to the applied voltage. In yet another implementation, pulse signals may be applied to the feedthrough assembly to detect defects.

In another embodiment, the method may include measuring of an insulation resistance of the insulating structure. In accordance with another embodiment, the method may include measuring a dielectric withstanding voltage of the insulating structure to assess whether a defect is present based on the results of the measurement.

Further aspects of the apparatus and the method of using the apparatus are disclosed herein. The features as discussed above, as well as other features and advantages of the present disclosure will be appreciated and understood by those skilled in the art from the following detailed description and drawings.

BRIEF DESCRIPTION OF THE DRAWINGS

The following drawings are illustrative of particular embodiments of the invention and therefore do not limit its scope, but are presented to assist in providing a proper understanding of the invention. The drawings are not to scale (unless so stated) and are intended for use in conjunction with the explanations in the following detailed description. The present invention will hereinafter be described in conjunction with the following drawing figures, wherein like numerals denote like elements, and.

DETAILED DESCRIPTION

The disclosure describes non-destructive electrical isolation assessment of an electrical feedthrough assembly for an implantable medical device. The feedthrough assembly provides an electrical circuit path extending from the interior of a hermetically-sealed housing for the implantable medical device to an external point outside the housing while maintaining the hermetic seal of the housing. Such a feedthrough assembly must meet exacting standards in order to provide electrical isolation while at the same time forming a proper seal between the interior of the housing and the external environment.

The non-destructive assessment of the present disclosure is utilized to quantitatively identify internal and external defects in the structure of the feedthrough assembly. The defects may arise from the raw materials utilized for manufacture of the components of the feedthrough assembly, during manufacture of the components, or even the assembly of the feedthrough assembly into the implantable medical device. Examples of the defects may include bubbles that are trapped within an insulating structure or foreign materials on or embedded within the insulating structure and other flaws or damage to the structure.

Figure 1:
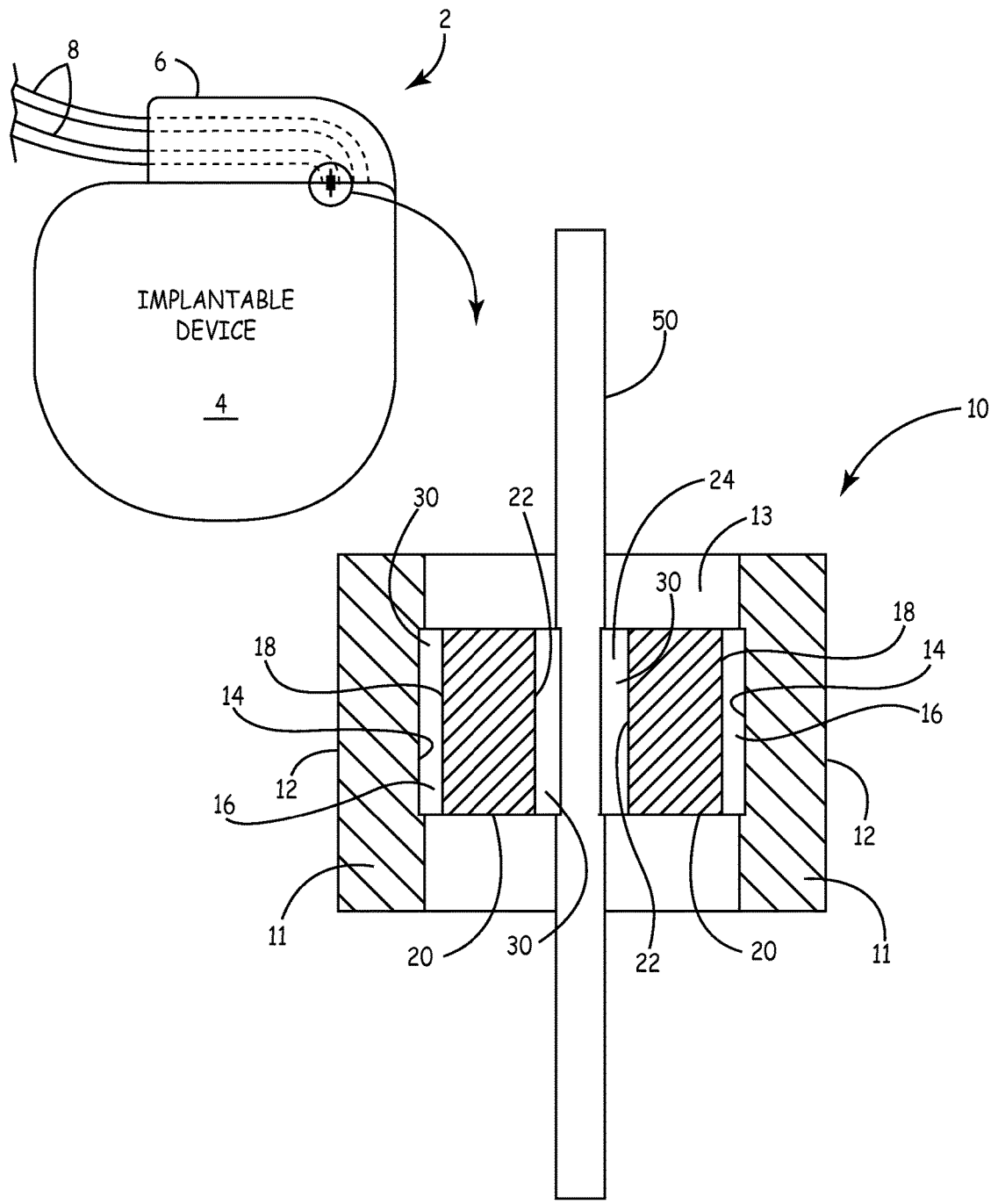
FIG. 1 is an exemplary implantable medical device incorporating a feedthrough assembly according to some embodiments.

Referring to FIG. 1, an exemplary implantable medical device 2 incorporating a feedthrough assembly 10 according to some embodiments is shown. Medical device 2 generally includes a housing 4 having a connector module 6 coupled thereto. Connector module 6 electrically couples various internal electrical components (not shown) located within housing 4 to external operational and/or diagnostic systems (not shown) located distal to device 2 through use of leads 8. Electrical connection of leads 8 to the internal electrical components is accomplished through use of feedthrough assembly 10.

An exemplary feedthrough assembly 10 according to the present teachings may include a ferrule 11, a terminal pin 50 (e.g. a pin), and an insulating structure 20. Ferrule 11 includes a ferrule outer surface 12, and a ferrule inner surface 14 that defines an inner lumen 13. Ferrule 11 may be brazed to insulating structure 20 and, therefore, is separated from insulating structure 20 by a ferrule-insulator interface 16. Insulating structure 20 includes an insulator outer surface 18 and an insulator lumen surface 22 that defines an aperture. The aperture defined by the insulator lumen surface 22 is formed having a first diameter that is sized to receive the terminal pin 50. The size of the diameter of the insulator lumen surface 22 may correspond to the diameter of the terminal pin 50, or may be larger relative to the diameter of the terminal pin 50. Insulating structure 20 may be brazed to terminal pin 50 and, therefore, may be separated from terminal pin 50 by an insulator-terminal pin interface 24. Interfaces 16 and 24 are filled with braze material 30.

While the exemplary embodiment in FIG. 1 shows a cross-section of a cylindrical insulating structure 20, a cylindrical ferrule 11, and a cylindrical terminal pin 50, other shapes can be envisioned and the present teachings should not be limited thereto. Further, although only a single terminal pin 50 is illustrated, it should be understood that feedthrough assembly 10 may include a ferrule 11 disposed about a plurality of terminal pins 50 as shown in U.S. Pat. No. 8,160,707 issued to Iyer et al and entitled "Method and Apparatus for Minimizing EMI Coupling in a Feedthrough Array Having at Least One Unfiltered Feedthrough," incorporated herein in its entirety. Other implantable feedthrough assemblies useful in the present teachings include those described in U.S. Pat. Nos. 7,164,572, 7,064,270, 6,855,456, 6,414,835 and 5,175,067, 5,735,884, 4,678,868, and U.S. Patent Application Publication No. 2006/0247714, all commonly assigned and all incorporated herein in their entireties.

Ferrule 11 may be formed of a conductive material and is generally adapted to secure feedthrough assembly 10 to housing 4. In some embodiments, the conductive material may be a metallic material including titanium, niobium, platinum, molybdenum, tantalum, zirconium, vanadium, tungsten, iridium, rhodium, rhenium, osmium, ruthenium, palladium, and any combination thereof. Ferrule 11 may have any number of geometries and cross-sections so long as ferrule 11 is an annular structure defining a lumen therein to receive the insulating structure 20. In some embodiments, ferrule 11 may surround insulating structure 20 and provide ferrule lumen surface 14 to contact braze material 30 disposed in the ferrule-insulator interface 16 to form a hermetic seal.

Ferrule 11 is typically laser welded to the IMD housing 4. Ferrule 11 may be provided with a welding flange such as that shown in the '707 patent to facilitate welding of ferrule 11 to the IMD housing when ferrule 11 is placed in an opening of housing 4. Ferrule 11 may be hermetically joined to an IMD housing by other welding methods, or even soldered or glued.

Insulating structure 20 may be formed from a material including an inorganic ceramic material (e.g., sapphire), a glass and/or a ceramic-containing material (e.g., diamond, ruby, crystalline aluminum oxide, and zinc oxide), and an electrically insulative material. Insulating structure 20 may also be formed of liquid-phase sintered ceramics, co-fired ceramics, a high-temperature glass, or combinations thereof. Insulating structure 20 may also include a sputtered thin niobium coating at least at surfaces 18 and 22. Because the sputtered niobium coating is thin, the coating is not shown for illustration purposes. Insulating structure 20 is not limited to any particular configuration for use in feedthrough 10, so long as insulating structure 20 includes an aperture that accommodates one or more electrically terminal pins 50.

Terminal pin 50 may be formed of materials such as iridium, molybdenum, niobium, palladium, platinum, tantalum, titanium, tungsten, and combinations thereof. Braze material 30 may be formed of a material such as gold. Other materials sufficient to braze ferrule 11 to insulating structure 20, and sufficient to braze insulating structure 20 to terminal pin 50, however, are contemplated. For example, braze material 30 may include materials such as high purity gold, and gold alloys containing silver, copper, tin, and/or zinc without departing from the spirit and scope of the present teachings. Alternatively, braze material 30 may comprise a material having a melting point less than melting points of ferrule 11, terminal pin 50, and insulating structure 20.

Feedthrough assembly 10 provides an electrical circuit pathway extending from the interior of hermetically-sealed device housing 4 to an external point outside housing 4 while maintaining the hermetic seal of the housing 4. The fluid tight hermetic seal is formed by metal braze 30 disposed in ferrule-insulator interface 16 and insulator-terminal pin interface 24 formed between the insulating structure 20 and the ferrule 11 and between the insulating structure 20 and terminal pin 50, respectively. A conductive path is provided through feedthrough 10 by terminal pin 50, which is electrically insulated from housing 4.

In the exemplary embodiments of the present teachings, biocompatible, non-conductive, high-temperature insulators 20 are provided for use in feedthrough assemblies 10 used, for example, in implantable electronic medical devices 2. As stated above, medical devices 2 may include implantable pulse generators for cardiac pacemakers that provide electrical stimulation to an arrhythmic heart or neural tissue, implantable defibrillators, implantable cardioverters, implantable cardiac pacemaker-cardioverter-defibrillators (PCD), implantable chemical/biochemical sensors (e.g., glucose sensors), cochlear implants, implantable drug-medicament or metabolite delivery devices (e.g., insulin pumps), and implantable medical devices that perform in vivo diagnostic monitoring and telemetry. Insulating structure 20 can be made from an electrically non-conductive high-temperature material, preferably a ceramic material, or combination of non-ceramic materials coated with, or having an outer layer comprising ceramic materials. In exemplary embodiments, insulating structure 20 may comprise alumina, silica, boron nitride, diamond, glass, ruby, sapphire, zircon, zirconia, zirconia toughened alumina, silicon nitride, silicon carbide, silicon oxide, and combinations thereof. A material of special interest is co-fired alumina, where a ceramic package comprised of electrically insulating alumina and electrically conductive refractory metal such as iridium, niobium, palladium, tantalum, titanium, platinum, tungsten, molybdenum, or combinations thereof, is sintered in one common step forming a hermetic system. In such an insulating structure 20, the terminal pin 50 need not be brazed to insulating structure 20 because the electrically conductive refractory metal serves as terminal pin 50.

For feedthrough assembly applications, a hermetic seal between the terminal pin 50, insulating structure 20, and ferrule 11 is desired. Since the reliability of implantable medical device 2 depends in large part on hermetic sealing of the components of the feedthrough assembly 10, the integrity of such seals is of paramount importance. In general, the insulating structure 20 may be formed separately from the other components of the feedthrough assembly 10 and subsequently bonded utilizing braze material 30.

The independent formation of the insulating structure 20 or the tasks involved in the assembly of the feedthrough assembly 10 may introduce defects that impact the performance and hermetic sealing of the feedthrough assembly 10. The defects within or on the surface of the insulating structure may include air bubbles trapped within or foreign materials overlaying or embedded on the surface. In accordance with embodiments of this disclosure, non-destructive electrical isolation assessments of the feedthrough assembly 10, and in particular, assessments to detect defects in the insulating structure 20 are performed to identify the presence of such defects. Therefore, the feedthrough assembly 10 is provided having the capacity to withstand the electrical isolation assessments.

Figure 2:
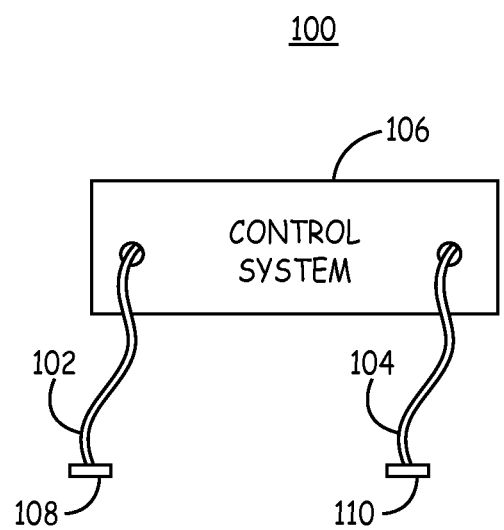
FIG. 2 shows a perspective view of a test probe that is operable to perform an electrical isolation assessment of a feedthrough assembly.

Reference is made to FIG. 2 for a general description of a system utilized to perform an electrical isolation assessment of a feedthrough assembly such as feedthrough assembly 10. By way of example, the details of the assessment will be described in the context of being performed on an insulating structure such as the insulating structure 20. However, the assessment should be understood as being applicable to other components of the feedthrough assembly.

FIG. 2 shows a perspective view of a test probe 100 that is operable to perform an electrical isolation assessment of the feedthrough assembly. Test probe 100 may be integrated with other components of a non-destructive assessment system (not shown) or into one or more components of an assembly line (not shown) that is utilized in the manufacture of implantable medical devices.

Test probe 100 includes at least two probe leads 102, 104 that are electrically coupled to a control system 106. A proximal end of each of the probe leads 102, 104 is coupled to the control system 106. Each of the probe leads 102, 104 may include one or more electrodes 108, 110 coupled to a distal portion of the lead. The electrodes 108, 110 may be configured to be engageable with a surface of the insulating structure. For example, the electrodes 108, 110 may be formed with corresponding surface area and geometry as the top and bottom portions of the insulating. In another example, the electrodes 108, 110 may each be formed with a pointed tip to engage only a small section of the surface area of the top or bottom portion of the insulating structure.

In one embodiment, test probe 100 is utilized to measure a dielectric property of the insulating structure at one or more test vectors. Electrodes 108, 110 establish the test vectors that are defined by the placement of the electrodes 108, 110 at different locations on the surface of the insulating structure. The test vectors are modified by moving the electrodes 108, 110 to different locations on the surface of the insulating structure. In this embodiment, the electrical isolation assessment is performed by generating a plurality of pulse signals by the test probe 100 and applying the pulse signals to the insulating structure through the electrodes 108, 110. This implementation may facilitate a localized assessment of the insulating structure to determine the presence of defects within a given location.

Alternatively, the pulse signals may be applied between mutually insulated portions of the feedthrough assembly 10 (FIG. 1). An example is the ferrule 11 and terminal pin 50 that are mutually insulated by the insulating structure 20. The electrodes 108, 110 may be coupled to the ferrule 11 and the terminal pin 50, respectively for application of the pulse signals to measure the dielectric property.

The pulse signals may be generated having a positive, a negative, or both positive and negative polarities. In one non-limiting example, a first series of a plurality of positive polarity pulses, e.g., ten pulses, may be generated followed by a second series of a plurality of negative polarity pulses, e.g., ten pulses, with a predetermined time interval being defined between each of the individual pulses and each series of pulses. Variations in the values of the measured dielectric at two or more locations where the measurements are performed are detected and a determination of the presence of defects is made responsive to the detected variation in the dielectric measurements.

The control system 106 includes a pulse signal generator (not shown) that generates the pulse signals that are applied to the insulating structure for the assessment. The signal generated by the control system 106 may include a sinusoidal waveform in the form of a radiofrequency signal or a non-sinusoidal waveform such as a pulse waveform having a plurality of pulses of one or either polarity, or a single high voltage pulse. Irrespective of the type of pulse signal chosen, the electrical characteristics of the signal are such that it enables detection of differences in the dielectric of an insulating structure. As a non-limiting example, the pulse signal generated by the pulse signal generator may include a radiofrequency signal having a frequency, for example, between 1 KHz and 2 MHz. However, it should be noted that a pulse signal having any suitable frequency may be utilized with the specific value being selected as a function of the material properties of the insulating structure, for example.

Control system 106 may further include a detector (not shown) that receives an electrical signal from the insulating structure responsive to the applied pulse signal. The detected electrical signal may be utilized to derive the dielectric of the insulating structure at a location defined between the probe electrodes 108, 110. Measurement of the dielectric properties across two or more locations on the insulating structure facilitates detection of defects in the insulating structure.

In an alternative approach, the control system 106 may alternatively, or additionally, be utilized to generate a high voltage pulse that is applied to the insulating structure to detect the presence of defects. The value of the high voltage pulse is based on the dielectric breakdown voltage of the insulating structure material. In accordance with the present disclosure, the voltage value of the high voltage pulse is programmed at a value that is less (between 1% to 15%, for example) relative to the actual breakdown voltage.

The inventors of the present disclosure have theorized that an insulating structure having defects will breakdown when a voltage having a value that is less than the actual breakdown voltage of the material is applied. A table of some examples of the dielectric breakdown field strength for different materials is provided below.

| Dielectric strength (in MV/m, or $10^6$ Volt/meter) of exemplary materials: | |
|---|---|
| Substance | Dielectric Strength (MV/m) |
| Sappire | 17.0 |
| Alumina (99.9%) | 13.4 |
| Aluminum silicate | 5.9 |
| Ruby - Mica | 118 |
| Fused Silica | 470-670 |
| Thermoplastic polymers | 15-24 |
| PolyRuby | |
| Fused silica | 25-40 at 20° C. |
| Barium Titanate (glass bonded) | >30 |
| Glass-filled melamine | 13.4 |
| Glass-filled allyl | 15.7 |

Referring to Table 1, the high voltage pulse implemented to detect the presence of a defect in glass, for example, will be programmed at a value ranging from 85% to 99% of the dielectric strength shown in the Table 1.

Alternatively, the breakdown voltage of materials other than those listed in Table 1 above, or components that are formed of composite materials of two or more compounds, may be determined experimentally by performing a test sequence that yields the breakdown voltage value.

Experiment

An example of such a test was conducted by the inventors of the present disclosure on a sample group of 70 electrically insulating structures that include materials such as glass, alumina or other ceramics. The test was performed on each of the samples in the following sequence. The insulating structure was subjected to a 1300 volt pulse with a 1000 v/usec rise time, 18 msec dwell and 1000 v/usec decay. Ten (10) positive polarity pulses and 10 negative polarity pulses were applied to an insulating structure between each terminal pin and ferrule. The parts were then tested with the same pulse sequence with increments of 100 volt amplitude added until breakdown was achieved. Of the sample group, 66 insulating structures passed the assessment and four insulating structures failed the test. The results of the testing were compared with a visual observation that was performed to identify failing parts prior to the electrical isolation assessments.

The results of the electrical isolation assessments indicated that there was a correlation with the results of the visual inspection. Specifically, the 4 insulating structures that were deemed to be defective, and hence failed the visual inspection, were also identified by the electrical isolation assessments as failing. This correlation confirmed the accuracy and reliability of the electrical isolation assessment in identifying the presence of a defect in the insulating structures. In addition, the non-failing insulating structures established a baseline of the breakdown voltage of the insulating structures. That is, the voltage at which the 4 insulating structures conducted (at which voltage the other 66 insulating structures did not conduct) could be used for subsequent assessments to identify insulating structures having unacceptable defects.

In an alternative embodiment, an electrical isolation assessment is performed by measuring the insulation resistance of the insulating structure. For example, a measure of the insulation resistance of the insulating structure is performed by coupling a suitable probe to the insulating structure. A comparative assessment of the resulting ohmic value that is measured may be performed by comparing the measured value against pre-determined values of a suitable ohmic range.

Yet another implementation of an electrical isolation assessment includes the measurement of the leakage current during a dielectric withstanding voltage test. In this example, the insulating structure is coupled to a test vehicle that generates a high voltage across the insulating structure. The high voltage may be greater than the dielectric withstanding voltage for a given material (such as the values shown in Table 1). In response to application of the high voltage, the leakage current of the insulating structure may be measured. Acceptable leakage current levels may be predefined with the measured leakage current being compared to the predefined leakage current to determine whether a defect is present.

In another embodiment, control system 106 may include a tuned resonant circuit (equivalent circuit shown in FIG. 3) to detect the presence of defects in the insulating structure. The tuned resonant circuit of the control system 106 may be in the form of an LRC, where L is inductance, R is resistance and C is capacitance. Such a tuned resonant circuit is tuned to resonate at a predetermined frequency provided by a sinusoidal signal generator. The tuned resonant circuit may be driven and interrogated by an analyzing tool such as an LCR meter, a spectrum analyzer, a network analyzer or any other suitable analyzing tool including, for example, a digital oscilloscope, an ohmmeter, a network analyzer, etc., any of which may comprise the control system 106.

The interrogation of the initially tuned resonant LRC circuit with an insulating structure subsequently coupled thereto provides a measure of the change in the characteristics of the tuned resonant circuit. The characteristics of the resonant circuit will change responsive to the coupling of the dielectric of the insulating structure. Responsive to the leads being coupled to two or more locations of the insulating structure, the magnitude of the changes in the resonant circuit characteristic may vary based on the presence of defects in the insulating structure. The defects in the insulating structure are manifested as variations in the magnitudes of change in the resonant circuit. As such, defects in the insulating structure may be detected based on the differences in the dielectric properties at various sections of the insulating structure that are introduced into the tuned resonant circuit in the form of capacitance that causes the changes in the characteristics of the previously tuned resonant circuit.

A spectrum of frequencies may suitably be applied to an insulating structure for characterization—that is, to obtain the tuned resonant circuit for the insulating structure. Alternatively, a spectrum of frequencies may be applied to the insulating structure to determine the frequency at which resonance will be achieved. A predefined resonating frequency may be provided for the material of the insulating structure. As such, the predefined resonating frequency may be compared to the applied frequency at which resonance is achieved. A deviation of the applied frequency from the applied frequency may provide an indication of the presence of a defect of the insulating structure.

Figure 3:
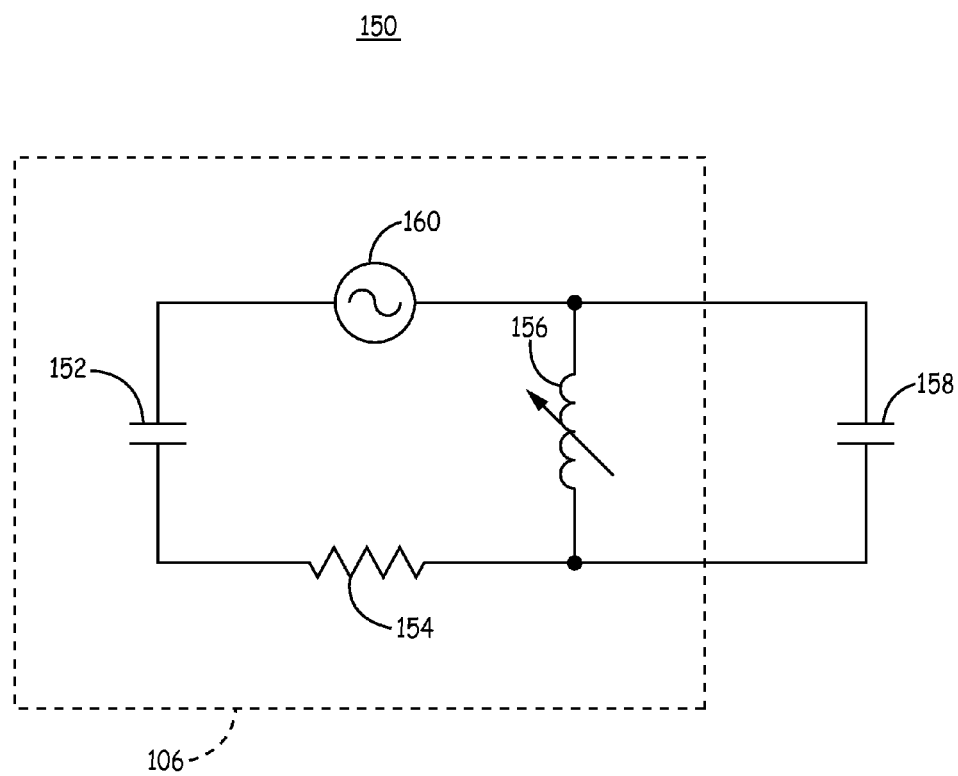
FIG. 3 depicts the equivalent circuit formed by a tuned resonant circuit in a control system of the test probe for the electrical isolation assessment of a feedthrough assembly.

Turning to FIG. 3, the equivalent circuit 150 formed by the tuned resonant circuit of the control system 106 when coupled to the insulating structure is shown. In particular, the components of the tuned resonant circuit include a capacitor 152, a resistor 154, a variable inductor 156, and a sinusoidal signal generator 160. The sinusoidal signal generator 160 provides a signal to the circuit components that causes resonance at a predetermined frequency. Together the capacitor 152, resistor 154, and inductor 156 form the LRC circuit. The capacitor 152 or inductor 156 may be provided as variable capacitor or inductor to facilitate tuning of the LRC circuit to a particular resonant frequency. By varying the value of the capacitor or the inductor, the LRC circuit may be impedance-matched to the analyzing tool.

Capacitor 158 represents the capacitance of the insulating structure at the contact points of the electrodes (e.g., 106, 108 in FIG. 2). The capacitance value of capacitor 158 changes in response to the defects that may be present in the insulating structure. In use, the LRC circuit is coupled to two or more locations on the insulating structure to detect differences in the magnitude of the change in the tuned resonant circuit characteristics. In other words, the magnitude of change in the characteristics will be uniform (or have a variation that is below a predetermined threshold value) for an insulating structure that has no defects. However, an insulating structure that has detectable defects will cause changes in the tuned resonant circuit having differing magnitudes (that may exceed a predetermined threshold value as will be discussed further below). The variation in the magnitudes depends on whether the contact points are at the location(s) of the defects in the insulating structure or at the non-defective location(s).

Figure 7:
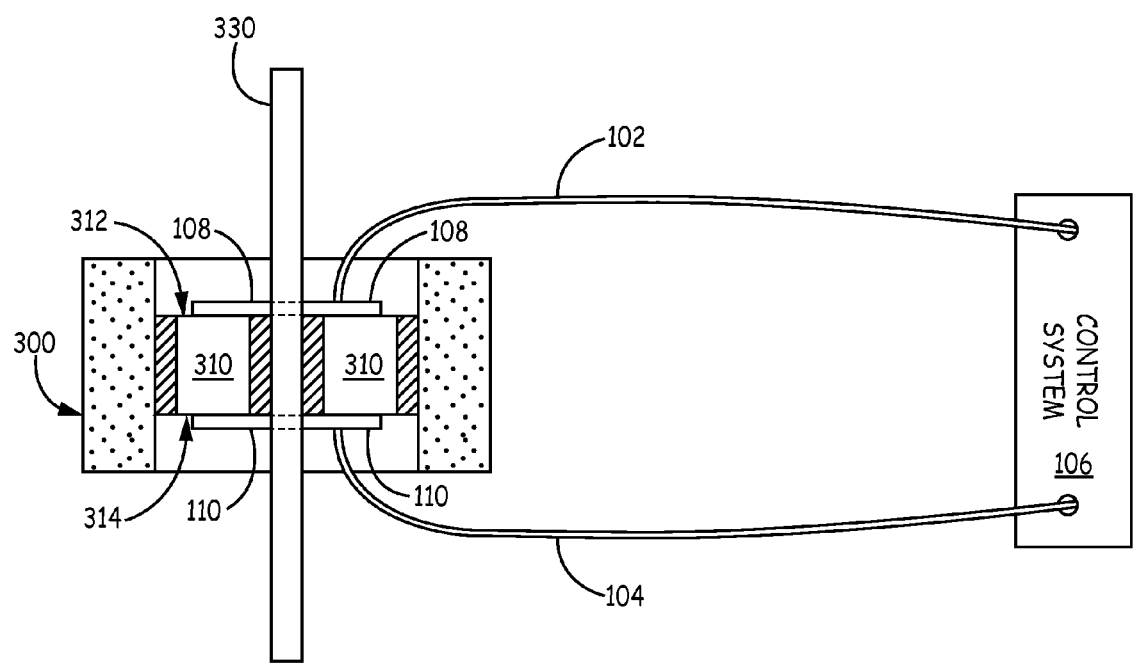
Figure 8:
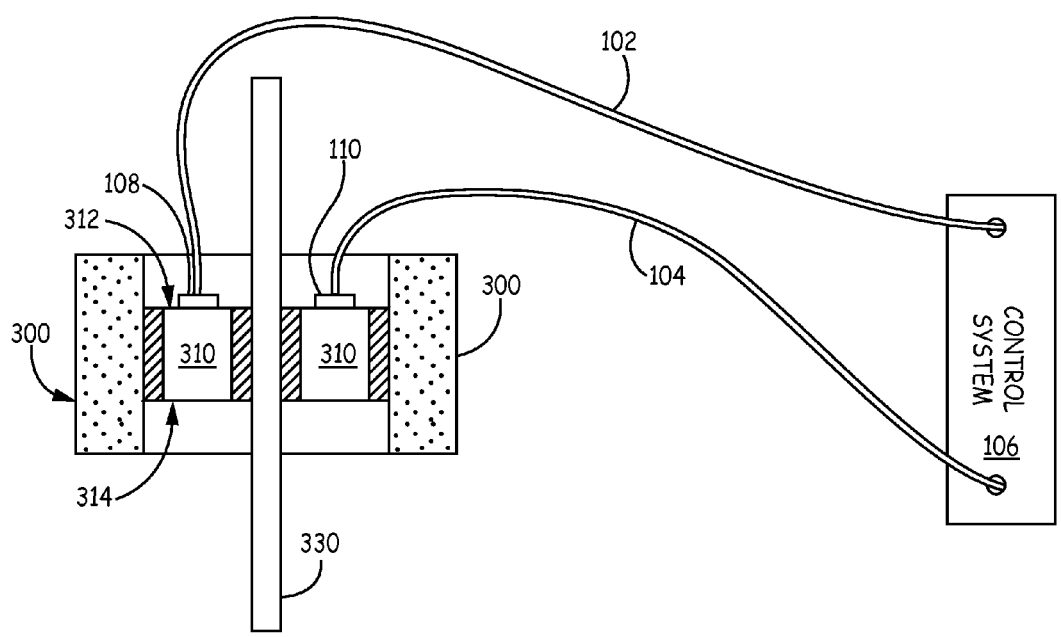
Figure 9:
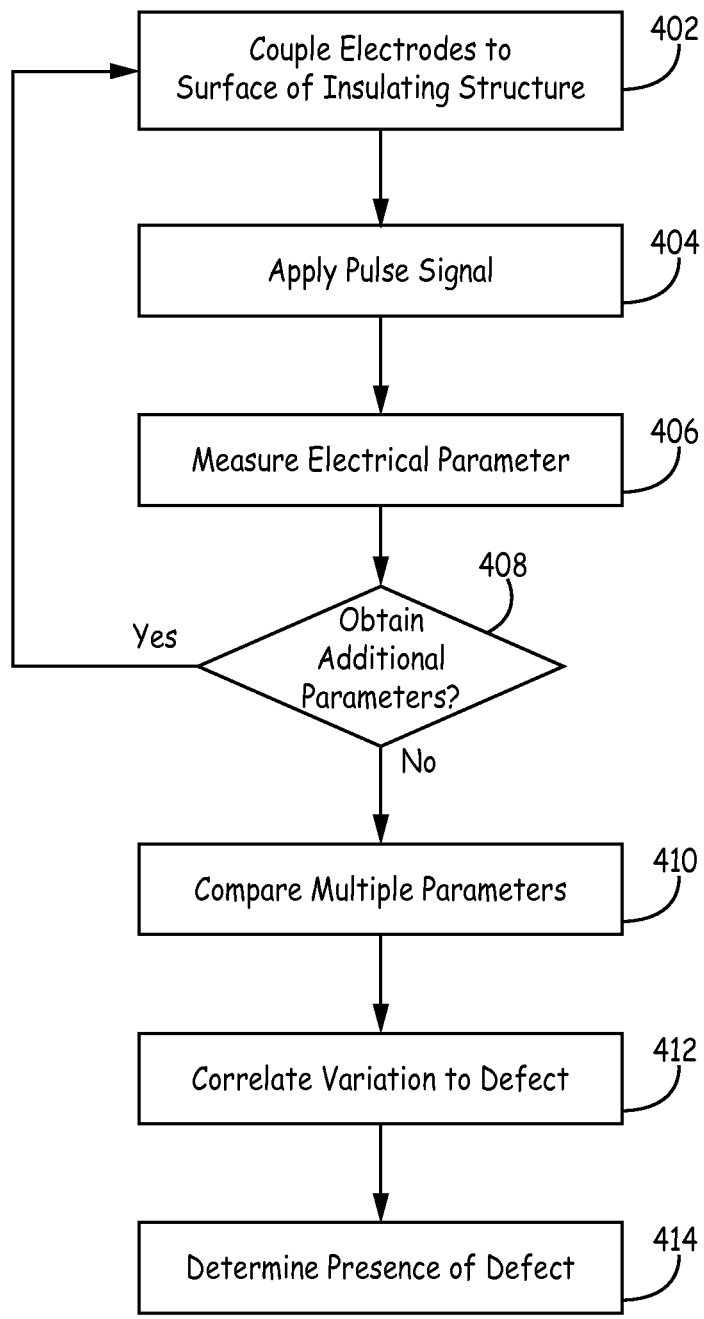
FIG. 9 is a flowchart summarizing the tasks included in a subset of method tasks of manufacturing the implantable medical device according to FIGS. 4-8.

FIGS. 4-9 depict a method 300 of manufacturing an insulating structure of an implantable medical device according to various embodiments of the present disclosure. FIG. 9 is a flowchart summarizing the tasks included in a subset of the method tasks of manufacturing the insulating structure of an implantable medical device according to FIGS. 4-8.

Figure 4:
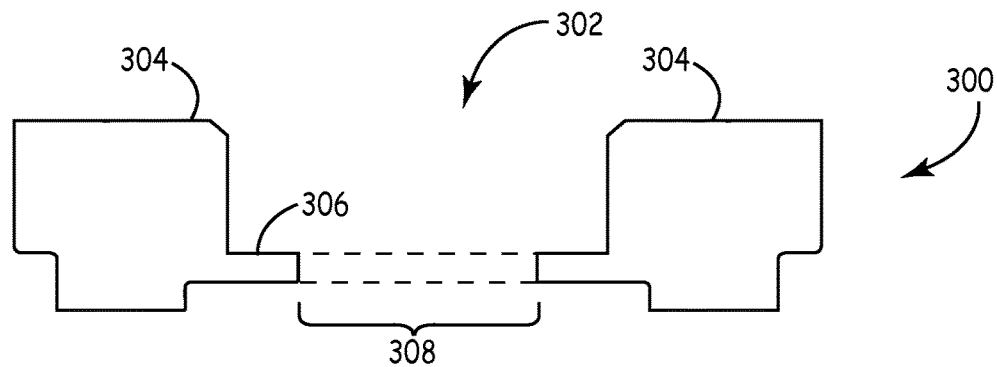
FIGS. 4-8 depict a method of manufacturing an insulating structure of an implantable medical device according to various embodiments of the present disclosure.
Figure 5:
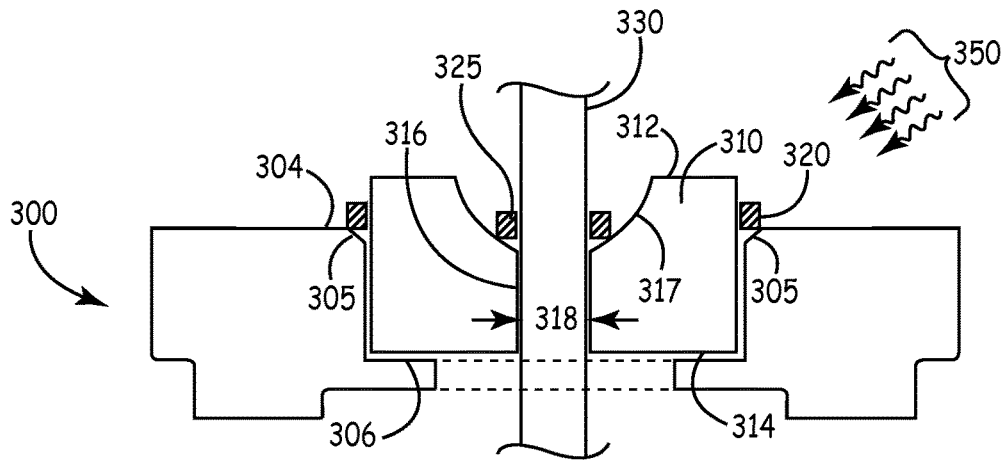
Figure 6:
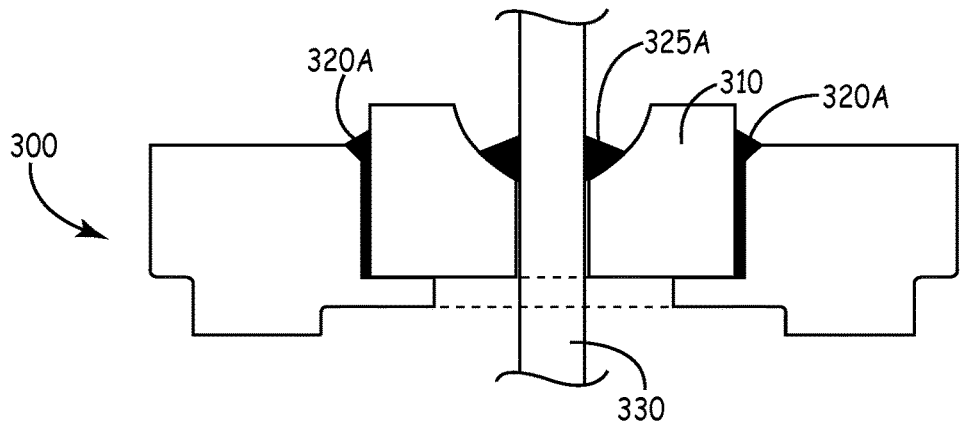

Turning to FIGS. 4-6, a ferrule 300 can include a recessed portion 302 in which an insulating structure 310 can be inserted. The recessed portion 302 can be bordered by wall portions 304 and further include a ledge 306 upon which an inserted insulating structure 310 can be placed such that the insulating structure 310 abuts the ledge 306. The recessed portion 302 can also define an opening 308 through which a terminal pin 330 can extend.

Insulating structure 310 can include a top portion 312, a bottom portion 314 and an inner lumen surface 316 that defines an aperture 318 extending from the top portion 312 to the bottom portion 314. In various embodiments, insulating structure 310 can include an angled portion 317 that assists with the bonding of the terminal pin 330 with insulating structure 310, as described more fully below.

In various embodiments of the present disclosure, the insulating structure 310 is inserted into the recessed portion 302 and the terminal pin 330 is inserted into aperture 318. A glass preform 320 can be fitted around insulating structure 310, and a second glass preform 325 can be fitted around terminal pin 330. In various embodiments, a chamfer 305 can be included in wall portions 304 to more securely position the glass preform 320 adjacent insulating structure 310. Further, angled portion 317 can be included in the insulating structure to more securely position the glass preform 325 adjacent terminal pin 330.

Upon application of heat 350, glass preform 320 will soften or partially or completely melt and flow into the recessed portion 302 between insulating structure 310 and wall portions 304. In this manner, glass preform 320 will form a glass seal 320A that fixedly secures the insulating structure 310 to ferrule 300, as illustrated in FIG. 6. Different types of energy (e.g., radiation, microwave, magnetic) can be utilized instead of, or in addition to, heat 350, depending on the composition of the preform utilized. The same or similar method can be utilized to create glass seal 325A between terminal pin 330 and insulating structure 310. In other embodiments, one of glass seals 320A, 325A may be used in combination with a gold braze or other sealing compositions (such as, glass seal 320A utilized with a gold braze to seal terminal pin 330 with insulating structure 310, or glass seal 325A utilized with a gold braze to seal ferrule 300 with insulating structure 310). In various embodiments of the present disclosure, the glass preforms 320, 325 and glass seals 320A, 325A can be formed of the glass composition described in U.S. Pat. No. 8,288,654 to Taylor, which is incorporated herein by reference in its entirety.

One or more non-destructive assessments, such as those described herein, may subsequently be performed on the insulating structure. In particular, the assessments include electrical isolation assessments that are performed to detect the presence of defects in the insulating structure. The defects may have been present on the constituent components prior to, or may be introduced during, the performance of manufacturing tasks. FIGS. 7-8 depict these method tasks and are described in conjunction with the flowchart in FIG. 9.

FIG. 7 depicts one embodiment of the electrical isolation assessment wherein the electrode 108 is electrically coupled to the surface of the top portion 312 and electrode 110 is electrically coupled to bottom portion 314 of the insulating structure 310 (402). The arrangement of the electrodes 108, 110 coupled to opposing surfaces of the insulating structure 310 effectively creates a capacitance. Each electrode may be spaced apart or electrically insulated from the terminal pin 330 and ferrule 300 to prevent short circuiting.

The configuration of FIG. 7 is suitable for identifying defects that are present within the insulating structure 310. Such defects may include bubbles that are trapped within the insulating structure 310 or other impurities that may affect the performance of the insulating structure 310. Without intending to be bound by theory, capacitance of the insulating structure—specifically across the path defined by the points of contact of the electrodes 108, 110 at the top portion 312 and bottom portion 314, respectively—is coupled to the tuned resonant circuit to cause the resonant circuit to no longer be tuned. Interrogating the resonant circuit provides a measure of the effectively added capacitance, which correlates to the dielectric properties at the electrode 108, 110 point of contact with the insulating structure 310 surface.

In another embodiment depicted in FIG. 8, the electrodes 108, 110 are both electrically coupled to the surface of the top portion 312 of insulating structure 310 (402). Nevertheless, the assessment may also be performed on the bottom portion 314, in which case both electrodes 108, 110 would be electrically coupled to the surface of the bottom portion 314 or any other desired portion of the insulating structure 310. In an embodiment, the electrodes 108, 110 may be coupled to the ferrule 11 and terminal pin 50, respectively. While not intended to be limiting, the assessment configuration of FIG. 8 may be useful in detecting impurities such as foreign materials that are deposited on the surface of the insulating structure 310 or overlaying the surface of the insulating structure 310.

Next, a pulse signal may be applied across the electrodes 108, 110 (404). In one embodiment, the pulse signal may include a non-sinusoidal waveform or a sinusoidal waveform. Without intending to be limiting, examples of the types of waveforms that may be utilized include a radiofrequency signal having a frequency in the range of 1 KHz to 1 MHz. Another example may include a pulse signal having a non-sinusoidal waveform, such as a single high voltage pulse having a voltage in the range of 500 volts to 2000 volts. The specific high voltage used in a given implementation may be selected as a function of the breakdown voltage of the insulating structure 310. Yet another example of the pulse signal may include a signal having a non-sinusoidal waveform of a plurality of pulses with a positive polarity, or a negative polarity, or both polarities. For example, the pulse signal may include a signal having a series of a plurality of positive pulses (e.g., ten) followed by a series of a plurality of negative pulses (e.g., ten), each individual pulse being separated from the preceding pulses by a predetermined interval.

An electrical parameter is subsequently measured (406) through the electrodes 108, 110 responsive to the applied pulse signal to obtain a measurement of the dielectric of the insulating structure 310. The measured electrical parameter may include insertion loss, capacitance, inductance, and ESR or any other parameter from which the dielectric of the insulating structure 310 may be derived.

In some embodiments, more than one electrical parameter measurement may be desired for comparative analysis of the dielectric properties at multiple locations of the insulating structure. If such measurement is desired, another surface may be selected for application of the pulse signal (408). The application of the pulse signal may be repeated with the electrodes 108, 110 being positioned at a different location on the insulating structure 310 to obtain a subsequent measurement of the dielectric at the measurement location. In such embodiments, the dielectric values measured across different locations of the insulating structure 310 are compared (410) to determine the presence of a variation in the dielectric values—the variation in the dielectric values indicates that there is a defect in the insulating structure 310.

In some embodiments, the defect is deemed to be present when the variation of the dielectric values at different locations exceeds a threshold limit. For example, the threshold limit may be set at a value within the range of 1% to 10%. One such threshold limit may be selected at 5%, and a defect is deemed to be present in response to the variation across different locations exceeding the 5%.

In another embodiment, test probe 100 (FIG. 2) may comprise a tuned resonant circuit, such as a RLC circuit, driven by a sinusoidal signal with a predetermined frequency provided by a sinusoidal signal generator. The coupling of the electrodes 108, 110 to the test probe 100 causes the tuned resonant circuit to resonate at a frequency that is different from the predetermined frequency. The resonant circuit can be interrogated to obtain an indication of the change in the circuit characteristics, such as a change in the frequency, of the formerly tuned resonant circuit in response to coupling the electrodes 108, 110 to the insulating structure 310. Two or more test vector may be defined, with the placement of electrodes 108, 110 on the insulating structure 310 being changed to the locations defined by the test vectors to obtain multiple measurements of frequency resulting from connecting the electrodes 108, 110 until a desired number of parameters is obtained (408). In this embodiment, a comparative analysis is performed for the measured parameters (410). Any variations in the magnitude of the change in the tuned resonant circuit characteristic (e.g., frequency) when the electrodes 108, 110 are coupled to two or more locations of the insulating structure are measured. The variations in the change are directly correlated to the presence of defects in the insulating structure 310 (412).

In other embodiments, the measurement of the electrical parameter may simply be to determine whether conduction is present (414) when the pulse signal is applied. Monitoring is performed between electrode 108 and electrode 110 to identify the presence of conduction. The electrodes 108, 110 are spaced apart, but both coupled to the insulating structure 310. The conduction will provide an indication that the dielectric properties of the insulating structure 310 have been impacted owing to the presence of a defect, and hence the material of the insulating structure becomes conductive at a voltage lower than the breakdown voltage. Therefore, the conduction of the applied signal may inherently provide an indication of a defect. This is because the applied signal is not expected to be conducted across the insulating structure 310, owing to its electrical non-conductivity, because the applied voltage is lower than the breakdown voltage of insulating structure 310.

Although the assessment has been described in the context of the test probe 100 (FIG. 2), it should be understood that any other apparatus that is capable of generating the aforementioned pulse signals or permitting measurement of the mentioned electrical parameters may be utilized. The present disclosure provides short duration quantitative electrical isolation assessments that are repeatable and predictable. Utilizing the electrical isolation assessments in accordance with embodiments of this disclosure increases the efficiency of detecting defects while improving the quality of the feedthrough assemblies.

While exemplary embodiments have been presented in the foregoing detailed description, it should be appreciated that a vast number of variations exist. It should also be appreciated that exemplary embodiments are not intended to limit the scope, applicability, or configuration of the invention in any way. Rather, the foregoing detailed description will provide those skilled in the art with a suitable road map for implementing embodiments of the invention. It may be appreciated that various modifications and changes can be made without departing from the scope of the invention as set forth in the appended claims.

What is claimed is:

1. A method of manufacturing a feedthrough assembly, comprising:
    providing an insulating structure having a top portion, a bottom portion and at least one aperture extending from the top portion to the bottom portion, the aperture having a first diameter;
    providing a ferrule having an outer surface, the ferrule defining an inner lumen surface;
    disposing the insulating structure within the inner lumen surface to fixedly secure the insulating structure to the ferrule;
    inserting a terminal pin into the aperture, the terminal pin having a diameter sized to correspond to the first diameter;
    performing an electrical isolation evaluation of the insulating structure, wherein the evaluation comprises applying a pulse signal between the terminal and the ferrule at one of the top portion and the bottom portion using a first electrode and a second electrode, wherein the first electrode is engaged with a surface along the top portion and the second electrode is engaged with a surface along the bottom portion; monitoring for occurrence of electrical conduction in response to the application of the pulse signal, wherein the presence of conduction provides an indication of a foreign material disposed on the insulating structure;
    measuring a first electrical parameter through the two electrodes responsive to the applied pulse signal;
    comparing the first electrical parameter to criteria for detecting foreign material;
    detecting foreign material on one of the top portion and the bottom portion in response to the first electrical parameter meeting the criteria for detecting foreign material;
    moving at least one of the two electrodes to a different location along the one of the top portion and the bottom portion;
    applying a next pulse signal using the two electrodes; and
    measuring a second electrical parameter in response to the next pulse signal;
        wherein comparing the first electrical parameter to criteria for detecting foreign material comprises comparing the first electrical parameter to the second electrical parameter to determine a variation in the first electrical parameter and the second electrical parameter and comparing the variation to a threshold, and
        wherein detecting the foreign material on the one of the top portion and the bottom portion comprises detecting the foreign material when the variation is greater than the threshold.

2. The method of manufacturing the feedthrough assembly of claim 1, wherein the pulse signal is characterized by a voltage that is less than a breakdown voltage of the insulating structure.

3. The method of manufacturing the feedthrough assembly of claim 2, wherein the insulating structure is evaluated to assess presence of conduction through the insulating structure in response to the applied pulse signal having the voltage that is less than the breakdown voltage of the insulating structure.

4. The method of manufacturing the feedthrough assembly of claim 1, wherein the presence of conduction provides an indication of a foreign material disposed within the insulating structure.

5. The method of manufacturing the feedthrough assembly of claim 1, wherein the pulse signal is characterized by a voltage in the range of 900 volts to 1700 volts.

6. The method of manufacturing the feedthrough assembly of claim 1, wherein the applied pulse signal comprises a plurality of positive pulses and a plurality of negative pulses, with a predetermined interval being provided between the delivery of each of the pulses.

7. The method of manufacturing the feedthrough assembly of claim 1, wherein the insulating structure is selecting having properties to provide electrical isolation between the terminal pin and the ferrule.

8. The method of manufacturing the feedthrough assembly of claim 1, further comprising brazing the lumen surface and at least a portion of the outer surface with a braze material.

9. The method of manufacturing the feedthrough assembly of claim 1, further comprising coupling the outer surface of the ferrule to the implantable medical device.

10. The method of manufacturing the feedthrough assembly of claim 1, further comprising coupling the ferrule to a housing of an implantable medical device.

11. The method of manufacturing the feedthrough assembly of claim 1, further comprising providing a sealing material to fixedly-secure the terminal pin with the insulating structure.

12. The method of manufacturing the feedthrough assembly of claim 1, further comprising providing two test probe electrodes having a surface area and geometry corresponding to the one of the top portion and the bottom portion and applying the pulse signal to the one of the top portion and the bottom portion by engaging both of the two test probe electrodes with a surface of the one of the top portion and the bottom portion.

13. The method of manufacturing the feedthrough assembly of claim 1, further comprising:
applying the pulse signal by:
engaging both the first electrode and the second electrode with the surface of the respective one of the top portion and the bottom portion at which the pulse signal is being applied, and
applying the pulse signal across the first electrode and the second electrode that are both engaged with the surface; and
monitoring for the presence of the electrical conduction through the first electrode and the second electrode.

* * * * *